United States Patent [19]

Chamberlin, Sr.

[11] Patent Number: Plant 6,044

[45] Date of Patent: Oct. 27, 1987

[54] PLUM TREE, MIDNIGHT SUN

[75] Inventor: Thomas O. Chamberlin, Sr., Visalia, Calif.

[73] Assignee: H. P. Metzler & Sons, Del Rey, Calif.

[21] Appl. No.: 802,357

[22] Filed: Nov. 27, 1985

[51] Int. Cl.[4] ..... A01H 5/03

[52] U.S. Cl. ..... Plt./38

[58] Field of Search ..... Plt./38

*Primary Examiner*—Robert E. Bagwill

*Attorney, Agent, or Firm*—Worrel & Worrel

[57] ABSTRACT

A new and distinct variety of plum tree which is characterized by bearing fruit which has a black skin color and nearly white flesh, the fruit having exceptional handling and cold storage characteristics.

1 Drawing Figure

BACKGROUND OF THE INVENTION

The present invention relates to a new and distinct variety of plum tree which has been denominated by the varietal name "Midnight Sun" and which is a chance seedling of unknown parentage. "Midnight Sun" is characterized as to novelty by producing fruit which matures for harvest approximately Aug. 20 at Del Rey, Calif., and which further produces large, black plums having a white flesh and mild flavor and which are freestone by nature and exhibit excellent handling and shipping characteristics.

It has long been known that the purchase of fruits such as plums by consumers, is largely influenced by the exterior coloration and size. Thus, it has been understood that it would be desirable to provide a plum tree which would bear fruit having a commercially aesthetic appeal, such as that presented by the present invention, which can be brought to market late in the season to compete with fruits being marketed in the same season.

ORIGIN AND ASEXUAL REPRODUCTION OF THE NEW VARIETY

For many years, the applicant has sought to produce improved varieties of fruit trees for his employer, H. P. Metzler & Sons Company of Del Rey, Calif. Pursuant to his assigned duties to develop new and distinct varieties of fruit trees, the inventor has collected from the various ranches of this employer various amounts of mixed seeds from their plum trees, has germinated these seeds, and subsequently evaluated the resulting seedlings to determine whether any new and distinct varieties are superior to varieties heretofore known. The subject variety "Midnight Sun" was a chance seedling which was discovered using this procedure.

The inventor procured a lot of mixed seeds from his employer's Ranch No. 5 which is located near Del Rey, Calif., in the fall of 1979. The resultant progeny were subsequently planted in the H. P. Metzler & Sons Nursery in the spring of 1980. The applicant carefully observed the new seedlings and had an opportunity to evaluate the fruit produced thereby in the late summer of 1982. At that time, a seedling was identified as having the desirable characteristics of producing a large, black plum relatively late in the season, which had the particular qualities the applicant was seeking. Upon noting that this particular seedling had highly desirable characteristics, the inventor collected budwood from the parent tree in the fall of 1982 and thereafter budded seedling trees in the H. P. Metzler & Sons test area of the same nursery. These test seedlings were carefully observed and it was noted that the first fruit were produced on these trees in August, 1984, and then in the following August, 1985. In each instance, the fruit produced by the seedling trees was collected and subsequently tested to determine its handling and storage characteristics. The new variety displayed noteworthy handling and storage characteristics. The tests conducted indicated that the fruit of the subject tree can be stored in cold storage for three to four weeks with no deleterious effects noted. Furthermore, the fruit produced by the seedling trees by this asexual reproduction technique produced progeny which were found to possess the same distinctive pomological characteristics as that of the original seedling.

BRIEF DESCRIPTION OF THE DRAWING

The accompanying drawing is a color photograph of a characteristic twig bearing typical leaves, several plums showing their external coloration sufficiently mature for harvesting and shipment, two mature plums of the color when matured on the trees, the plum halved transversely in the suture plane to illustrate the flesh coloration, and several stones, all of the subject variety.

DETAILED DESCRIPTION

Referring more specifically to the pomological details of this new and distinct variety of plum tree, the following has been observed under the ecological conditions prevailing at the farm of H. P. Metzler & Sons Company located near Del Rey, Calif. All major color code designations are by reference to the Inter-Society Color Council, National Bureau of Standards. Common color names are also employed.

TREE

Size: Medium.

Figure: Upright growth, depending upon pruning practices.

Vigor: Vigorous.

Productivity: Noteworthy.

Regularity of bearing: Excellent.

Trunk:

*Thickness.*—Average.

*Surface texture.*—Average plum bark.

*Color.*—Medium Brown, (58 m. Br.).

*Lenticels.*—Approximately 16 to 18 per square inch.

*Lenticel size.*—Average.

Branches:

*Size.*—Average.

*Surface texture.*—Average plum bark.

*Color.*—Medium Brown, (58 m. Br.).

*Lenticels.*—Approximately 16 to 18 per square inch.

*Lenticel size.*—Average, approximately 3/16 inch (4.762 mm.) in length.

LEAVES

Size: Large.

*Length.*—Approximtely $3\frac{1}{2}$ to 4 inches, (88.9 through 101.6 mm.).

*Width.*—Approximately $1\frac{1}{2}$ to $1\frac{3}{4}$ inches, (38.1 to 44.45 mm.).

*Shape.*—Lanceolate; the leaves of the subject variety are quite wide in the center of the leaf but taper sharply in the last $\frac{3}{4}$ inch (19.05 mm.), to form a narrow point.

*Color — dorsal surface.*—(125 M. 01. G).

*Color — ventral surface.*—(120 m.y. G.).

*Marginal form.*—Doubly serrate.

*Shape of glands.*—Globose.

*Size of glands.*—Quite small, approximately 1/16 inch, (1.588 mm.).

*Color of glands.*—(102 m.g.y.).

*Petiole.*—Length — approximately 3/16 inch, (4.762 mm.). Thickness — approximately 1/16 inch, (1.588 mm.).

*Stem glands.*—Number — one pair. Arrangement — opposite to each other.

*Stipules.*—None evident.

Flower buds:

*Size.*—Length — approximately $\frac{1}{4}$ inch (6.35 mm.). Diameter — approximately 3/16 inch, (4.762 mm.). Shape — slightly elongated.

*Petiole.*—Length — approximately $\frac{1}{4}$ inch, (6.35 mm.); this petiole length is determined at a time prior to the opening of the bud.

*Bud development.*—Each bud appears to develop by itself.

*Color.*—Dull Green (120 m.y.g.); this color is determined at a time prior to any white color appearing at the apex of the bud.

Flowers:

*Date of first bloom.*—Feb. 25 through Mar. 1 at Del Rey, Calif. This date of bloom is just prior to the bloom of Santa Rosa Plum Tree at the same location.

*Petal length.*—Approximately 5/16 inch, (7.938 mm.).

*Petal diameter.*—Approximately 3/16 inch, (4.762 mm.).

*Petal shape.*—Nearly round.

*Color.*—White (#263 White).

*Flower development.*—Each blossom develops by itself; the buds of the subject variety do not split to produce three flowers, as is characteristic of some plum varieties.

*Petiole.*—Approximately, 3/16 inch, (4.762 mm.); this length is determined when the blossoms are in full bloom.

FRUIT

Maturity when described: Ripe for harvesting; approximately Aug. 20 at Del Rey, Calif.

Size:

*Uniformity.*—Good.

*Axial diameter.*—Approximately $2\frac{3}{8}$ inches to $2\frac{1}{2}$ inches, (60.325 through 63.5 mm.).

*Diameter transverse in suture plane.*—Approximately 2 inches to $2\frac{1}{4}$ inches, (50.8 through 57.15 mm).

*Diameter transverse in cheek plane.*—Approximately $2\frac{3}{8}$ inches to $2\frac{1}{2}$ inches, (60.325 through 63.8 mm.).

Form:

*Uniformity.*—Uniform.

*Shape.*—Nearly round.

Suture: Very smooth.

*Suture length.*—Approximately $3\frac{1}{4}$ inches, (82.55 mm.); the suture extends from the base to the apex.

Ventral surface: Generally round.

Stem cavity: Variable, round to slightly elongated.

*Stem cavity depth.*—Approximately $\frac{1}{4}$ inch, (6.35 mm.).

*Base.*—Round, and nearly flat.

*Apex.*—Round.

*Pistil point.*—Slight; it appears almost receded.

Stem:

*Length.*—Approximately $\frac{1}{4}$ inch, (6.35 mm.).

*Thickness.*—Approximately 1/16 inch, (1.588 mm.).

Skin:

*Thickness.*—Generally less than 1/64 inch, (0.397 mm.).

*Surface texture.*—Very smooth.

*Tenacious to flesh.*—Yes.

*Tendency to crack.*—None observed.

*Color.*—Black (235 p. Black).

Flesh:

*Color.*—Nearly White, (89 p.y.).

*Texture of pit well.*—Slightly rough.

*Color of pit well.*—Yellowish-Brown, (72 d.oy.).

*Juice production.*—Very juicy.

*Flavor.*—Noteworthy; mild, with no hint of any acid taste.

*Aroma.*—Slight.

*Texture.*—Smooth and crisp.

*Fibers.*—None evident.

*Ripening.*—Even.

*Eating quality.*—Exceptional.

Stone:

*Free or cling.*—Nearly full freestone.

*Fibers.*—None evident.

*Color.*—Yellowish-Brown, (32 d. OY).

*Size.*—Length—approximately 162 inch, (22.225 mm.). Width — approximately 9/16 inch, (14.288 mm.). Thickness — approximately $\frac{3}{8}$ inch, (9.525 mm.).

*Form.*—Elongated.

*Base.*—Nearly pointed.

*Texture of sides.*—Nearly smooth; stone has a slightly rough texture.

*Ridges.*—None evident.

Use of the plum: Fresh market.

Storage qualities: Exceptional; the subject variety has been tested in cold storage and kept for periods in excess of three weeks with no deleterious effects noted.

Shipping quality: Noteworthy; the subject variety maintained exceptional firmness for extensive periods of time and therefore indicates that it has exceptional shipping characteristics.

Although the new variety of plum tree possesses the described characteristics as a result of the growing conditions in Del Rey, Calif., in the central part of the San Joaquin Valley, it is to be understood that variations of the usual magnitude in characteristics incident to growing conditions, fertilization, pruning and pest control are to be expected.

Having thus described my new variety of plum tree, I claim:

1. A new and distinct variety of plum tree substantially as illustrated and described, which is characterized as to novelty by producing fruit which is mature for harvesting approximately Aug. 20 at Del Rey, Calif., and which further bears a large, black plum which is nearly round in shape, having a nearly white flesh which has a mild, noteworthy flavor and which further displays exceptional handling and cold storage characteristics.

* * * * *

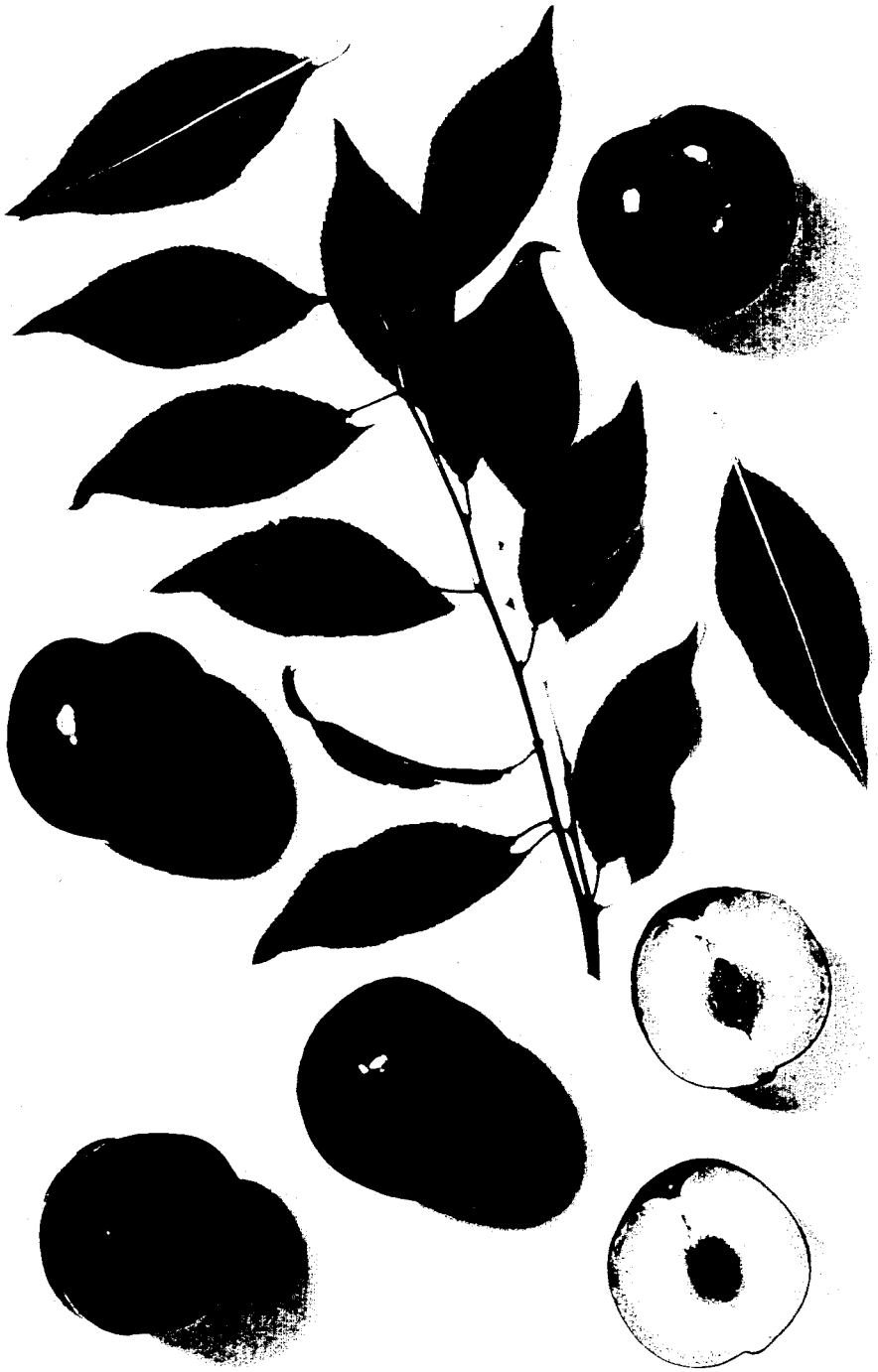

UNITED STATES PATENT AND TRADEMARK OFFICE

CERTIFICATE OF CORRECTION

PATENT NO. : PP06044

DATED : October 27, 1987

INVENTOR(S) : Thomas O. Chamberlin, Sr.

It is certified that error appears in the above-identified patent and that said Letters Patent is hereby corrected as shown below:

Column 4, line 57, delete "162" and substitute ---7/8---.

Signed and Sealed this

Twelfth Day of April, 1988

*Attest:*

DONALD J. QUIGG

*Attesting Officer*

*Commissioner of Patents and Trademarks*